US009624536B2

(12) United States Patent
Peumans (10) Patent No.: US 9,624,536 B2
(45) Date of Patent: Apr. 18, 2017

(54) MICROFLUIDICS SYSTEM FOR SEQUENCING

(71) Applicant: IMEC, Leuven (BE)

(72) Inventor: Peter Peumans, Herfelingen (BE)

(73) Assignee: IMEC, Leuven (BE)

( * ) Notice: Subject to any disclaimer, the term of this patent is extended or adjusted under 35 U.S.C. 154(b) by 903 days.

(21) Appl. No.: 13/875,922

(22) Filed: May 2, 2013

(65) Prior Publication Data

US 2013/0296174 A1    Nov. 7, 2013

(30) Foreign Application Priority Data

May 2, 2012  (EP) .................................. 12166483

(51) Int. Cl.

| C12M 1/00 | (2006.01) |
|---|---|
| C12M 1/34 | (2006.01) |
| C12M 3/00 | (2006.01) |
| C12Q 1/68 | (2006.01) |
| G01N 15/06 | (2006.01) |
| G01N 33/00 | (2006.01) |

(Continued)

(52) U.S. Cl.
CPC .......... *C12Q 1/6869* (2013.01); *B01L 3/5027* (2013.01); *B01L 3/502707* (2013.01); *B01L 2300/0816* (2013.01); *B01L 2300/0864* (2013.01); *B01L 2300/0874* (2013.01); *B01L 2300/0887* (2013.01); *B01L 2400/0487* (2013.01)

(58) Field of Classification Search
CPC .. B01L 3/50; C12M 1/00; C12M 1/34; G01N 33/00; C12Q 1/68

USPC ............ 435/6.1, 283.1, 287.2, 288.4, 288.5; 422/68.1, 502

See application file for complete search history.

(56) References Cited

U.S. PATENT DOCUMENTS

| 6,167,910 B1 | 1/2001 | Chow |
|---|---|---|
| 2002/0012930 A1 | 1/2002 | Rothberg et al. |

(Continued)

FOREIGN PATENT DOCUMENTS

| GB | WO 2006/117541 | * 11/2006 |
|---|---|---|
| WO | WO2005/080606 A1 | 9/2005 |
| WO | WO2010/124001 A1 | 10/2010 |

OTHER PUBLICATIONS

European Search Report, European Patent Application No. 12166483.3 dated Nov. 5, 2012.

*Primary Examiner* — Narayan Bhat
(74) *Attorney, Agent, or Firm* — McDonnell Boehnen Hulbert & Berghoff, LLP (57) ABSTRACT

A microfluidic chip for use in multiplexed analysis of samples is described. The microfluidic chip comprises a plurality of sensing chambers and further comprises at least a first fluid supply channel for providing a first fluid and a plurality of microfluidic channels. These are in fluid communication with at least one sensing chamber and with the first fluid supply channel for delivery of said first fluid to the at least one sensing chamber. The microfluidic channels are branching off from the supply channel in the neighborhood of the sensing chamber that can be provided with the first fluid through the microfluidic channel. The different channels thus form a tree-like delivery distribution system for supplying the first fluid to said plurality of sensing chambers.

35 Claims, 4 Drawing Sheets

(51) Int. Cl.
*G01N 33/48* (2006.01)
*B01L 3/00* (2006.01)

(56) References Cited

U.S. PATENT DOCUMENTS

2002/0047003 A1* 4/2002 Bedingham .......... B01L 3/5025
  219/388
2005/0252773 A1 11/2005 McBride et al.

* cited by examiner

MICROFLUIDICS SYSTEM FOR SEQUENCING

CROSS-REFERENCE TO RELATED APPLICATIONS

This application claims the benefit of priority of European Patent Application no. 12166483.3, filed May 2, 2012, which is hereby incorporated herein by reference in its entirety.

BACKGROUND OF THE INVENTION

Field of the Invention

The invention relates to the field of sensing such as for example biosensing. More particularly, the present invention relates to methods and systems for multiplexed, i.e. simultaneous, sensing or characterizing samples in microfluidic devices, such as for example used in sequencing applications.

Technical Background

For a number of sensing applications, such as for example different biosensing applications, the need for multiplexed processing is high. In several applications, a large number of sensing events needs to be performed for obtaining an accurate characterization of a sample. One example of such an application whereby a large number of sensing events are required is sequencing. To obtain sufficiently efficient characterisation systems, there is a constant pressure from the market for increasing the number of sensing events that can be obtained with a microfluidic chip per day. In order to increase this number, the number of sensing sites can be increased. The density of sensing sites that can be introduced on a microfluidic chip can be high, e.g. more than $10^4$, more than $10^5$, more than $10^6$, etc.

Alternatively, for increasing the number of sensing events that can be obtained, also the time required for performing the sensing and making the chip again ready for further sensing can be shortened. Especially in case a washing step is required for preparing the chip for further use, such as for example in the case of sequencing by synthesis, the time required for getting the different fluids at the proper position may be an important factor influencing the overall time required for a sensing event. Although a number of different techniques have already been suggested for improving the time required for a sensing event, e.g. in a sequencing application, further improvement is needed if high speed processing, e.g. at a rate of at least 100 Gbp/day or even better at a rate of at least 300 Gbp/day.

In addition to increasing the speed of sequencing devices there is also a need to reduce the overall cost. A washing step contributes to higher costs as large amounts of reagents are needed in the case of sequencing by synthesis.

SUMMARY OF THE INVENTION

It is an object of embodiments of the present invention to provide a microfluid biosensing device, e.g. for sequencing, allowing multiplexed sensing or characterizing.

It is an advantage of embodiments of the present invention that a microfluidic biosensor with a high throughput can be obtained. It is an advantage of embodiments of the present invention that the washing time and reagents used for washing can be limited.

It is an advantage of embodiments of the present invention that the flow in at least different sets of microfluidic channels, and more advantageously in some embodiments in each of the microfluidic channels can be controlled independent from other micro-fluidic channels. It is an advantage of at least some embodiments that the flow in the micro-fluidic channels can be based on a negative pressure that is applied, e.g. in common, to the plurality of microfluidic channels, externally to the micro-fluidic chip.

It is an advantage of embodiments of the present invention that the distance to be traveled in the microfluidics network is small so that the amount of product required for operating the device can be small. The amount of product wasted therefore is reduced. It is an advantage of embodiments of the present invention that the amount of reagents required, e.g. for washing, can be limited: a general washing step for the complete chip is avoided, instead washing is performed per channel thereby reducing the amount of fluid.

It is an advantage of embodiments of the present invention that the microfluidic biosensing device can make us of densely positioned sensors, allowing a high throughput.

The above objective is accomplished by a method and device according to the present invention. The present invention relates to a microfluidic chip for use in multiplexed analysis of samples, the microfluidic chip comprising a plurality of sensing chambers and the microfluidic chip further comprising at least a first fluid supply channel for providing a first fluid, a plurality of microfluidic channels, each microfluidic channel being in fluid communication with at least one sensing chamber, whereby each of the microfluidic channels is in fluid communication with said first fluid supply channel for delivery of said first fluid from said supply channel to said at least one sensing chamber, the microfluidic channels branching off from the supply channel in the neighborhood of the sensing chamber that can be provided with the first fluid through the microfluidic channel, the different channels thus forming a tree-like delivery distribution system for supplying the first fluid to said plurality of sensing chambers. Different microfluidic channels may deliver to different sensing chambers.

The microfluidic channels may branch off from the supply channel at branch points such that for each sensing site, the branch point positioned closest to the sensing site is the branch point where the microfluidic channel for supplying that sensing site branches off of the supply channel.

The plurality of sensing chambers may be further in fluid communication with a waste channel.

The waste channel may be a common waste channel for said plurality of sensing chambers.

The supply channel on the one hand and the plurality of microfluidic channels on the other hand may be substantially positioned in a different layer of the microfluidic chip.

The fluid communication may be controllable using a valve.

The valve may be a valve positioned outside the microfluidic chip.

The microfluidic chip may be adapted for performing sequencing by synthesis, the microfluidic chip comprising four supply channels for delivery of four types of deoxyribonucleotide triphosphates and at least one supply channel for delivery of washing reagent, each supply channel comprising a set of microfluidic channels in fluid communication with said first fluid supply channel for delivery of said first fluid from said supply channel to said at least one different sensing chamber, the microfluidic channels branching off from the supply channel in the neighborhood of the sensing chamber that can be provided with the first fluid through the microfluidic channel.

The present invention also relates to a sensing system comprising a microfluidic chip reader and a microfluidic chip for co-operating with the microfluidic chip reader, wherein the microfluidic chip is a microfluidic chip as described above.

The present invention furthermore relates to a method for performing multiplexed analysis of samples based on microfluidics, the method comprising delivery of at least one fluid from a common supply channel, through a plurality of microfluidic channels towards the plurality of sensing chambers, whereby each microfluidic channel transports the fluid from the common supply channel to a sensing chamber and each of the microfluidic channels branches off in the neighborhood of the measurement site it can deliver fluid to, the channels thus forming a tree-like delivery distribution system for supplying the first fluid to said plurality of sensing chambers, and sensing an interaction between a component in the sensing site and a component delivered with the fluid.

The delivery of at least one fluid may comprise subsequent delivery of different deoxyribonucleotide triphosphates (dNTP), whereby for each delivery of a particular deoxyribonucleotide triphosphate, the delivery and the sensing may comprise adding a fluid comprising the particular deoxyribonucleotide triphosphate (dNTP) to each of the plurality of measurement sites by providing a flow of the fluid through a common supply channel and a plurality of microfluidic channels connected to the common supply channel towards each of the sensing channel at the sensing site, thus allowing interaction between the particular deoxyribonucleotide triphosphate and the sequence to be characterized at each sensing site, adding a fluid comprising washing reagent for washing each of the measurement sites, and sensing the interaction between the particular deoxyribonucleotide triphosphate and the sequence to be characterized for each measurement site.

For each delivery of a particular deoxyribonucleotide triphosphate (dNTP) said adding a fluid may comprise supplying the fluid with particular deoxyribonucleotide triphosphate (dNTP) through a different supply channel.

Adding a fluid may comprise washing reagent for washing each of the measurement sites comprises performing a washing step in predetermined microfluidic channels and not in other microfluidic channels.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to a microfluidic device, reference is made to a device wherein fluids are transported in one or more channels and whereby at least one of the dimensions of the one or more channels has a size between 100 nm and 10 µm.

Where in embodiments of the present invention reference is made to a microfluidic chip, reference may be made to a microfluidic device wherein measurements can be performed on microfluidic samples. Such a microfluidic chip may be a cartridge that can be used in a reader system for performing the sensing. It may be disposable, limited re-usable or re-usable.

In a first aspect, the present invention relates to a microfluidic chip for use in a system for multiplexed analyzing of samples. It thereby is an advantage of embodiments of the present invention that the microfluidic chip can provide a large number of measurements sites. In at least some embodiments of the present invention, the number of read locations can be $10^6$ or higher, although embodiments of the present invention are not limited thereby. The microfluidic chip may for example be especially suitable for performing sequencing, such as sequencing by synthesis. The microfluidic chip according to embodiments of the present invention comprises at least a first common fluid supply channel for providing a first fluid to a plurality of measurement sites. The microfluidic chip according to embodiments of the present invention furthermore comprises a plurality of microfluidic channels whereby each microfluidic channel is being in fluid communication with at least one sensing chamber at the measurement site. Each microfluidic channel furthermore is in fluid communication with said first fluid supply channel for controllable delivery of said first fluid to said at least one sensing chamber. In this way, the channels form a tree-like delivery distribution system for supplying the first fluid to said plurality of sensing chambers. By providing a tree-like delivery distribution system, which could also be referred to as a hierarchical distribution system and which comprises a supply line with branched of microfluidic channels for different measurements sites, the distances to be traveled by the fluids can be reduced, resulting in a speed up of the delivery. The microfluidic channel branching off of the common supply channel may branch off of the common supply channel at a position in the neighborhood of the measurement site to which it supplies the fluid. The microfluidic channel may be branching off at a branching point on the common supply channel closer to the measurement site than other branching points are positioned to the measurement site. In some embodiments the microfluidic channel may be branched off at a position as close as possible to the measurement site. The latter results in the fluid being as long as possible transported in a common supply channel, so that the total length of channels to be introduced in the chip can be limited. In some embodiments, also the common supply channels may be branched off of a larger common supply channel, again rendering the total length of channels to be introduced in the chip limited. When multiple fluids are to be used, multiple tree-like delivery distribution systems can be provided on the same chip, providing efficient delivery of different fluids. The latter can avoid the need for washing the microfluidic structure to re-use it for another fluid. In one example, a system according to an embodiment of the present invention is especially suitable for e.g. sequencing by synthesis whereby a different tree-like delivery distribution system is provided for multiple fluids, e.g. for each of the four deoxyribonucleotide triphosphates (dNTP) to be added to the sensing chamber separately. Furthermore, one of the supply channels or an additional supply channel also may be adjusted—e.g. through connection with a reservoir for washing reagents—for delivery of reagents for washing so that efficient delivery of the washing reagents, and consequently, efficient washing can be obtained. In this way the flood and wash cycles can be speed up drastically, resulting in faster processing. The latter may in some embodiments result in a cycle time for sequencing by synthesis in the range 0.01 to 0.1 s.

Figure 1:
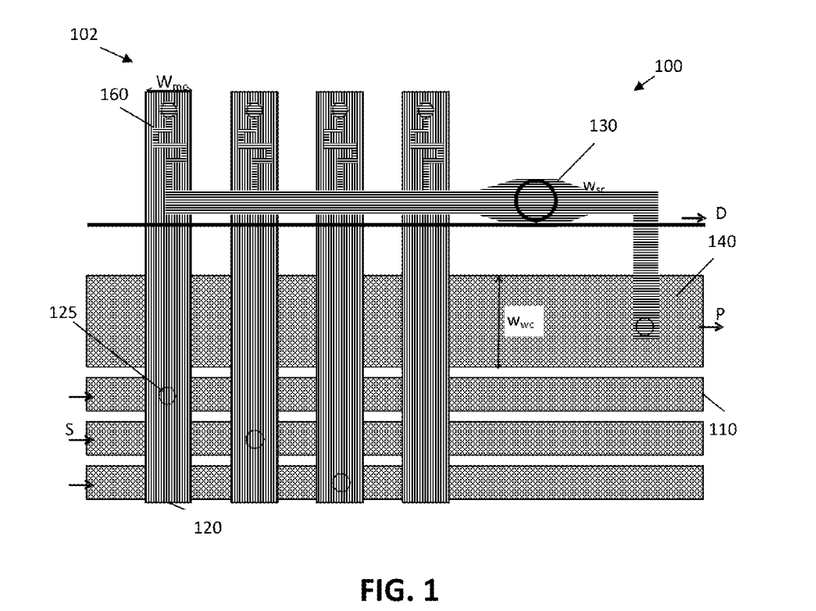
FIG. 1 illustrates a top view of the fluidic channels and the optical sensing element of a microfluidic chip according to an embodiment of the present invention.
Figure 2:
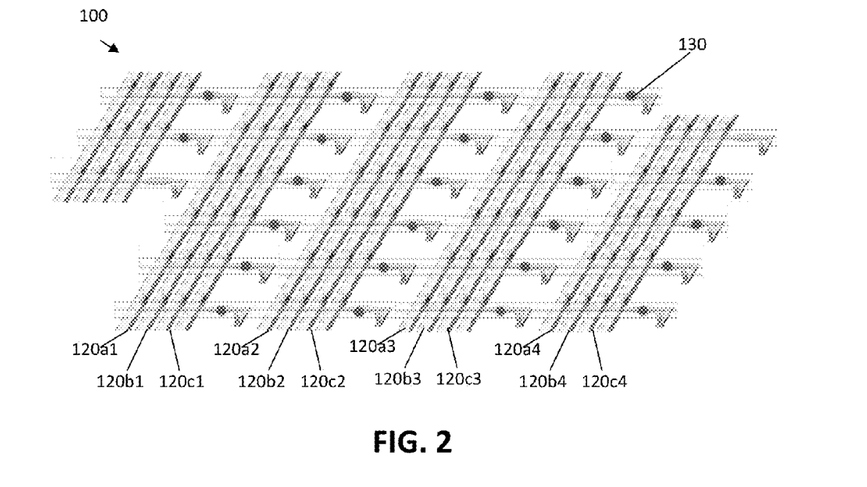
FIG. 2 illustrates part of a microfluidic chip according to an embodiment of the present invention.

By way of illustration, further features and advantages of at least some embodiments of the present invention are illustrated with reference to FIGS. 1 and 2 illustrating an exemplary microfluidic device according to an embodiment of the present invention.

FIG. 1 illustrates an enlarged view of a single microfluidic cell unit, i.e. a portion of the microfluidic cell correlated with one measurement site. FIG. 2 illustrates part of a microfluidic chip comprising a plurality of microfluidic cell units. Advantageously, according to embodiments of the present invention, the microfluidic chip comprises a large number of measurement sites. The number of measurement sites may be at least $5 \cdot 10^5$, advantageously at least $1 \cdot 10^6$. The latter provides the possibility to perform multiplexing. Especially for example in sequencing by synthesis, such multiplexing is required for obtaining the necessary efficiency.

In FIG. 1, part of the microfluidic chip 100 is shown, being a microfluidic unit cell 102 correlated with one measurement site. In the microfluidic unit cell 102, the supply channel 110 for providing a first fluid is indicated. In the present example a plurality of supply channels is visible, each supply channel being suitable for delivering a same or a different fluid. In one example, more than one supply channel may be used for allowing faster switching between supply of different fluids, as during the supply of a first fluid, in a separate supply channel already another fluid can be loaded. In a particular example, the number of supply channels 110 is selected such that separate supply channels are available for each of the four deoxyribonucleotide triphosphates (dNTP) to be delivered during sequencing by synthesis, as well as at least one, in the current example being two, separate supply channels 110 for washing steps to be performed during sequencing by synthesis. In other embodiments, some supply channels 110 can be used subsequently for different fluids to be delivered at each of the measurement sites, so that only a limited number of supply channels 110 is to be provided. In some embodiments, the supply channels 110 may be common to all measurement sites. In other embodiments, the supply channels 110 may be common to only a certain group of measurement sites, each group still comprising a plurality of measurement sites, rendering the supply of fluids still advantageous over individual supply channels for each measurement site.

According to an embodiment of the present invention, the supply channel 110 is in fluid communication with a plurality of microfluidic channels 120, each microfluidic channel supplying the fluid to a measurement site, or more particularly to a sensing chamber 130 thereof. The fluid communication may be performed by a branching point 125 being a via 125, as indicated in FIG. 1. In one example, the microfluidic channel 120 may comprise a portion that has a smaller cross-section than the remaining part of the microfluidic channel. Such a portion is shown by way of example by portion 160 in FIG. 1. In the present example, the portion with smaller cross-section is positioned in the same layer of the microfluidic chip wherein the sensing chamber 130 is situated where the sensing data is gathered, whereas the remaining part of the microfluidic channel is positioned in another layer of the microfluidic chip. The portion of the microfluidic channel having the smaller cross-section may be the end portion of the microfluidic channel 120, i.e. the portion 160 of the microfluidic channel 120 just upstream the sensing channel wherein the sensing chamber 130 is situated. This portion 160 may be the last portion of the microfluidic channel that is filled, before the step of filling the sensing chamber 130 is performed. The portion 160 of the microfluidic channel 120 may be adapted for acting as a fluidic stop under predetermined conditions, fulfilled when no fluid flow from the corresponding microfluidic channel is required. The latter may advantageously be used for avoiding contamination. Due to the fluidic stop, it can be prevented that fluid from this channel unintentionally enters the sensing channel while an other fluid is delivered. In order not to obscure FIG. 2, the one or more supply channels are not shown. According to embodiments of the present invention, a common supply channel is provided for supplying a fluid to microfluidic channels 120a1, 120a2, 120a3, 120b4 . . . . In the example shown, different common supply channels are present so that also a common supply channel is provided for supplying a fluid to microfluidic channels 120b1, 120b2, 120b3, 120b4, etc., and in a similar manner a common supply channel is provided for supplying a fluid to microfluidic channels 120c1, 120c2, 120c3, 120c4, etc. As indicated above, the advantage of providing a common supply channel is that a more efficient delivery can be provided, without the need for having a single supply microfluidic channel from reservoir to each measurement site separately.

According to embodiments of the present invention, the microfluidic chip also comprises sensing chambers, wherein characterisation—or the process allowing such characterisation—can be performed. Such characterisation can take a variety of forms. It can be based on the interaction between different fluids, it can be based on interaction of a fluid with a functionalized surface of the sensing chamber, it can be based on interaction of a fluid with a reagent being present in the sensing chamber, etc. The sensing technique used according to embodiments of the present invention may be based on any type of sensing mechanism, such as for example but not limited to optical sensing. In one embodiment, sensing may comprise sensing of a signal change due to a changed characteristic of the environment, e.g. through interaction of a component in the fluid with another component, e.g. present as component on a functionalized surface, in the sensing chamber. In one particular example, the sensing may comprise sensing a change in an optical signal in a ring resonator adjacent the sensing chamber or partly or fully in the sensing chamber. Advantageously, the sensing technique used allows for simultaneously sensing in a plurality of sensing chambers, in order to obtain an efficient sensing system.

The microfluidic chip furthermore may comprise a waste channel, through which, the fluid may be removed, e.g. after interaction of the fluid with a component in the sensing chamber—such as for example after binding or after washing—and/or after measurement. In one example, the waste channel is adapted with a first output through which the used fluid can be outputted. The latter can be performed in a spontaneous or a in a forced manner. Removal of the fluid may for example be performed by forcing the fluid out of the microfluidic chip. In one example this may for example be performed by pumping, e.g. inducing a negative pressure at the output side or inducing a positive pressure at the input side. In one example, the waste channel may be adapted with an opening through which the negative pressure can be induced. Typically, a pumping means or forcing means will not be part of the microfluidic chip, but rather be part of a sensing system or reader.

According to some embodiments, the fluidic communication between the supply channel and one, more or each of the plurality of microfluidic channels may be a controllable fluidic communication, i.e. it can be controlled whether fluid can flow from the supply channel to the microfluidic channel. In one embodiment, control regarding the flow can be obtained for each of the microfluidic channels communicating with a certain supply channel individually or groupwise. The latter can for example be performed by controlling a pressure at input or output of a fluidic channel of the microfluidic chip. Also in case more than one supply channel and corresponding microfluidic channel can deliver fluid to a same sensing chamber, the fluidic communication between these channel and the sensing chamber can be controlled individually or groupwise. In one set of embodiments, this may at least partly be controlled by controlling valves externally to the microfluidic chip. Such valves may be passive valves and/or active valves. Examples of valves that may be used are electronic valves, microfluidic stops, mechanical valves, MEMS-based valves, etc. The valve may for example be a Teflon valve.

By way of illustration embodiments of the present invention not being limited thereto, an example of a microfluidic chip is described below, the microfluidic chip being especially suitable for sequencing through synthesis. According to the example, the microfluidic chip comprises six supply channels, whereby two supply channels are provided for supplying reagents for washing and four supply channels are provided for supplying each of the four deoxyribonucleotide triphosphates (dNTP). For each of the sensing sites on the microfluidic chip, six different microchannels are provided, each one being in fluidic communication with a different one of the six supply channels, for delivering the reagents for washing and the reagents comprising one of the deoxyribonucleotide thrisphosphates to the sensing chamber. The different microfluidic channels can be incorporated such that these are positioned parallel next to each other such that only a width of about 9 µm is required (i.e. a width of 1 µm per channel and an interspacing of 0.5 µm between the channels). The different reagents, after interaction at the sensing site with the component to be characterized or after performing the washing step, are removed through a waste channel in fluidic communication with the sensing chamber. For controlling the fluid flow, at the end of the waste channel a negative pressure may be induced, resulting in combination with the thickness and shape of the fluidic channels in a diffusion time in the microfluidic channel for the fluid to be transported of 4 μs (influenced by a local pressure of 0.03 bar) and a diffusion time in the sensing channel and through the measurement chamber of 1 μs (influenced by a 0.008 bar local pressure). The overall size of the sensing site is small and the fluid flows are fast, resulting in one example of a microfluidic chip that can be used for efficient sequencing by synthesis.

In the present example, sensing is performed optically. When, in the neighborhood of a ring resonator an interaction occurs for example by binding of a target particle to be sensed, this alters the optical characteristic of the ring resonator. As a consequence, a shift in a resonating frequency of the ring resonator occurs. In the present example, this is used to detect a binding event. An optical signal thereby is fed through a waveguide positioned closely to the ring resonator so that coupling can occur when the frequency of the optical signal matches the resonating frequency of the ring resonator. The optical signal may be generated by a radiation source, which component typically is introduced in the sensing system. The coupled radiation or the remaining radiation can be sensed in a detector. For accuracy reasons also a reference ring resonator may be provided, allowing to provide a reference signal. The detected signal can then be processed for deriving a property or characteristic of the component based thereon.

It is an advantage of at least some embodiments of the present invention that the microfluidic chip can be fully manufactured (both microfluidic components and sensing components present in the chip) using one type of technology, e.g. using silicon-based technology. By way of illustration, an example of a manufacturing method for manufacturing an exemplary device of an embodiment of the present invention is discussed below with reference to FIG. 3a to FIG. 3e. In FIG. 3f an overview of the device is shown whereby the microfluidic channels of the cross-section are also shown in top view. It is to be noticed that this manufacturing process is only provided by way of illustration, embodiments of the present invention not being limited thereto.

Figure 3A:
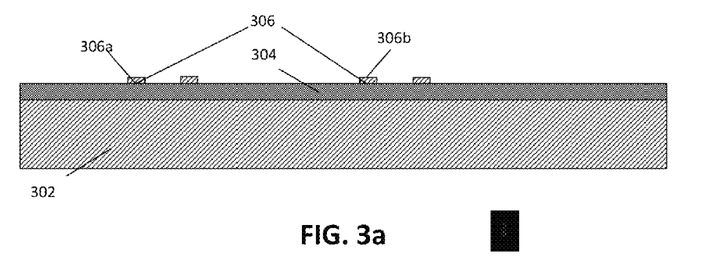
FIG. 3a to FIG. 3e illustrate different intermediate products obtained during a manufacturing process of a microfluidic chip according to an embodiment of the present invention.

In a first step, shown in FIG. 3a, a substrate is provided. According to the current example, the microfluidic chip is adapted for sensing using a change in an optical signal, and two ring resonators one being the sensor ring and one being the reference ring, which will not be close to or in contact with the sample, are provided. In a particular structure, this is obtained by providing a silicon substrate 302, providing a buried oxide layer 304 thereon and providing on top of the buried oxide layer the sensing system 306 comprising the reference ring 306a at one position and the sensor ring 306b at another position.

Figure 3B:
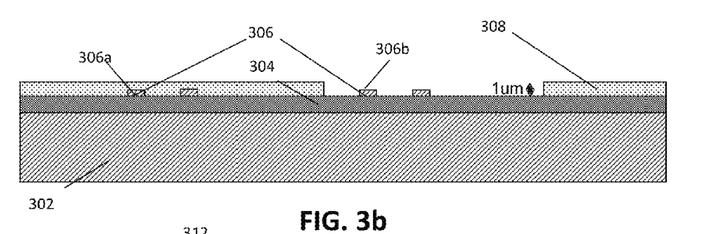

In a second step, shown in FIG. 3b, the reference ring 306a is covered by a top layer 308, whereas the sensor ring 306b is left uncovered. The thickness of the top layer 308 may for example be a 1 μm layer. In the above two steps, the sensing components of the microfluidic chip are manufactured. In the following steps, the microfluidic components of the microfluidic chip will be manufactured in a separate substrate that will be fixed to the substrate comprising the sensing components.

Figure 3C:
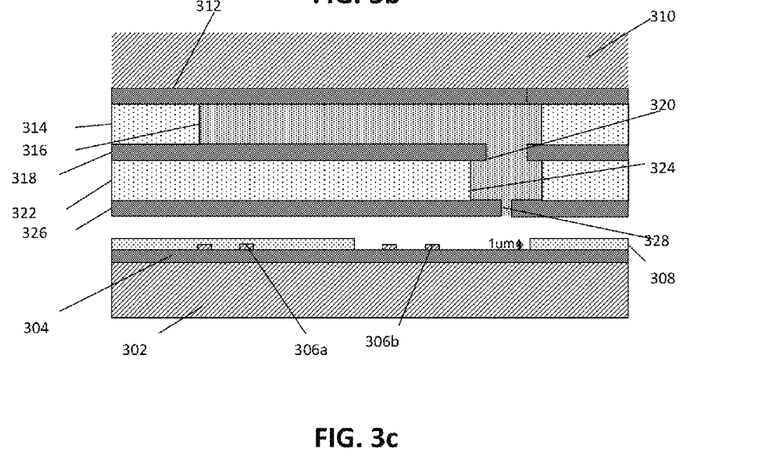

In a third step, illustrated in FIG. 3c, a second substrate comprising the microfluidic components is manufactured. The latter can be done using conventional silicon processing steps, such as layer deposition, masking steps, etc. The obtained second substrate comprises in the current particular example, a silicon substrate 310, covered with a silicon dioxide layer 312, a further silicon dioxide layer 314 wherein the space where the supply channel will be positioned is filled with sacrificial material 316 and a further silicon dioxide layer 318 wherein at the position where the via will be present sacrificial material 320 is provided. The second substrate furthermore comprises, on top of further silicon dioxide layer 318, another silicon dioxide layer 322 with sacrificial material 324 at the position where the first portion of the microfluidic channel will occur and finally yet another silicon dioxide layer 326 with sacrificial material 328 at the position where a further portion of the microfluidic channel will occur.

Figure 3D:
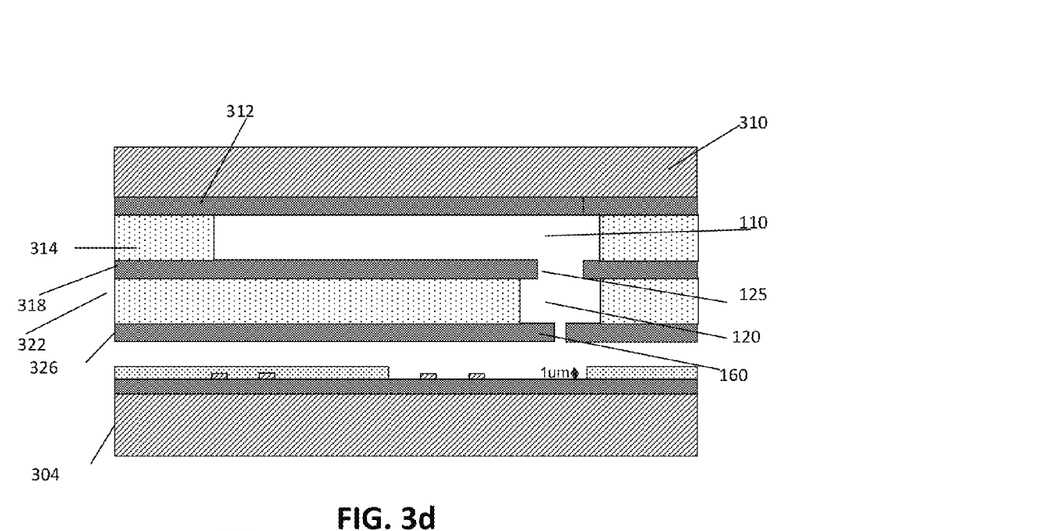

In a fourth step, illustrated in FIG. 3d, the sacrificial material is removed, e.g. through etching. This results in the microfluidic channels being formed. The cross-section of the first portion of the microfluidic channel thereby may for example be about 2 μm wide and between 2 and 5 μm in height.

Figure 3E:
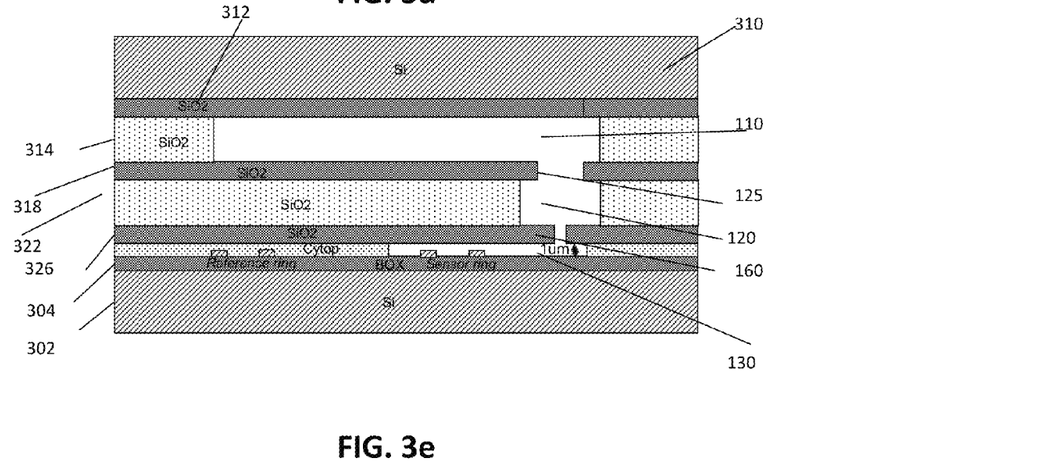
Figure 3F:
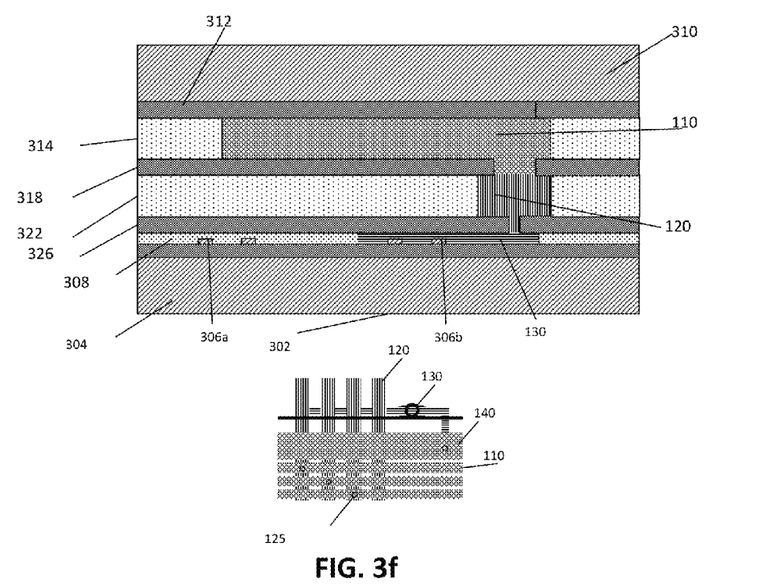
FIG. 3f illustrates a microfluidic chip with the different fluidic channels indicated in cross section (A) and a corresponding top view of the different fluidic channels according to an embodiment of the present invention.

In a fifth step, the two substrates are bound to each other resulting in the microfluidic chip of the present example, as illustrated in FIG. 3e. FIG. 3f shows the same microfluidic structure, whereby the microfluidic channels of the device are indicated with a particular pattern and whereby the microfluidic channels of the device are furthermore shown in top view, indicated with the same particular patterns.

Figure 4:
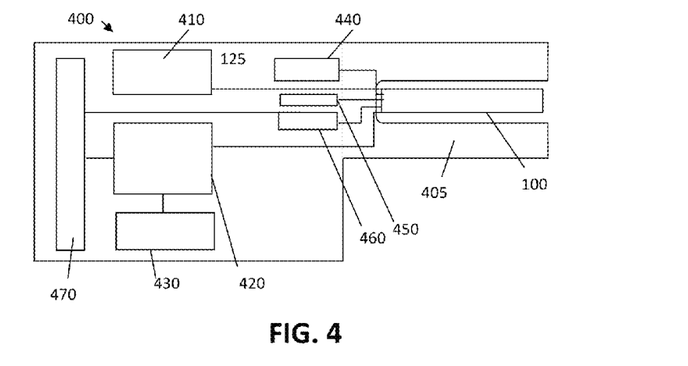
FIG. 4 illustrates a schematic representation of a sensing system according to an embodiment of the present invention.

According to one aspect, the present invention relates to a microfluidic sensor comprising a sensor system—sometimes also referred to as a chip reader—and a microfluidic chip as described in the first aspect, or comprising a sensor system adapted for co-operating with a microfluidic chip as described the first aspect. The sensor system may be adapted to receive the microfluidic system in a predetermined manner, so that optionally accurate connection with e.g. fluidic supplies to and from the microfluidic chip, ports for inducing a pressure in the chip, electrical contacts, optical connections, etc. can be obtained. In some embodiments, the sensor system may be adapted for receiving the microfluidic chip in a slot. More generally, the microfluidic sensor 400 may comprise a microfluidic chip holder 405 for holding the microfluidic chip 100.

The microfluidic sensor 400 according to embodiments of the present invention may comprise one or more fluidic storage compartments 410 from where one or more fluidic species can be delivered to the microfluidic chip 100. The microfluidic sensor furthermore may comprise a detecting means 420 for registering the signals, sensed in e.g. the sensing chamber. Such detecting means 420 may be based on an optical detector, a magnetic sensor, an acoustic sensor, an electrical sensor, a chemical sensor, etc. depending on the sensing technique used. If for example an optical technique is used, the microfluidic sensor—also referred to as sensing system—also may comprise a radiation source for providing radiation towards or in the microfluidic chip. Other components required for the detection that can be integrated in the sensing system, may be incorporated. The detecting means 420 may provide registered data to a processor 430 for processing the data. Such a processor 430 may be incorporated in the sensor or alternatively can be separate therefrom, e.g. not being part of the microfluidic sensor 400. The microfluidic sensor 400 furthermore may comprise a pressure inducing means 440, e.g. for generating a negative pressure to the microfluidic chip, such as for example a pumping means. Furthermore, optionally also valves 450 may be incorporated in the microfluidic sensor e.g. for controlling microfluidic flow in the microfluidic chip. Control sensors 460, e.g. for controlling accurate flow in the microfluidic chip, for controlling temperature in the microfluidic chip, . . . also may be included.

The microfluidic sensor 400 advantageously comprises a controller 470. Such a controller may for example be used for controlling and timing the flow of the one or more fluids to the measurement sites, e.g. in a particular order to perform an assay or e.g. to perform sequencing by synthesis, for controlling the sensing e.g. by controlling a radiation source and a detector in case optical sensing is performed, etc.

The microfluidic sensor 400 furthermore may comprise other features and components known by the skilled person from existing microfluidic sensors.

In another aspect, the present invention relates to a method for performing multiplexed analysis of samples based on microfluidics. Multiplexed analysis allows to simultaneously perform analysis at a number of measurement sites. Furthermore according to embodiments of the present invention, the multiplexed analysis can be performed in a fast manner, as providing the necessary fluids to the measurement sites can be performed in a fast manner due to a tree-like fluid delivery structure comprising a common supply channel and a plurality of microfluidic channels branched off of the common supply channel for delivering the fluid to the different measurement sites. The method according to embodiments of the present invention comprises delivery of at least one fluid from a common supply channel, through a plurality of microfluidic channels towards the plurality of sensing chambers, whereby each microfluidic channel transports the fluid from the common supply channel to a sensing chamber. Each of the microfluidic channels may branch off in the neighborhood of the measurement site it needs to deliver to, e.g. closer to the measurement site than other microfluidic channels branching off of the same common supply channel. The delivery of the fluid thus is based on a channel structure—comprising the common supply channel and the microfluidic channels—forming a tree-like delivery distribution system for supplying the first fluid to said plurality of sensing chambers. It thereby is an advantage of embodiments of the present invention that the overall length of fluidic channels to be provided on the chip can be reduced, as the delivery is based on a tree-like channel structure—also referred to as hierarchical channel structure. The delivery may be performed in a controlled manner. Controlling the delivery may comprise providing a negative pressure downstream the microfluidic channels, in order to induce a flow of the fluid. Controlling the delivery also may comprise controlling a number of valves for controlling the flow of fluids. Further features and method steps may express the functionality of components as described in the first aspect.

By way of illustration, embodiments of the present invention not being limited thereto, one embodiment will be described in more detail, wherein the method for performing multiplexed analysis is a method for performing sequencing by synthesis.

The exemplary method comprises, for a plurality of measurement sites, providing a sequence to be characterized at each of the measurement site. The method also comprises for each of the four deoxyribonucleotide triphosphates subsequently:

adding a fluid comprising the particular deoxyribonucleotide triphosphate (dNTP) to each of the plurality of measurement sites by providing a flow of the fluid through a common supply channel and a plurality of microfluidic channels connected to the common supply channel towards each of the sensing channel at the sensing site, thus allowing interaction between the particular deoxyribonucleotide triphosphate and the sequence to be characterized at each sensing site, adding a fluid comprising washing reagent for washing each of the measurement sites. The latter allows to remove the unbound material, so an accurate measurement of only the bound dNTPs is obtained, sensing the interaction between the particular deoxyribonucleotide triphosphate and the sequence to be characterized for each measurement site.

The sensing technique used may for example be based on optical detection, although embodiments of the present invention are not limited thereto, and e.g. electrical detection, chemical detection, acoustical detection, etc. can also be performed. Advantageously, different tree-like fluidic channels are provided for the different deoxyribonucleotide triphosphate (dNTP) supplied. Adding a fluid comprising washing reagent for washing may be performed using the same common supply channel and microfluidic channel structure as for the particular deoxyribonucleotide triphosphate (dNTP) to be washed away, i.e. by flowing the washing fluid subsequently through the same channels. Alternatively, supply of the washing fluid may be performed from a separate supply channel and microfluidic channel structure, i.e. such a separate structure may be used for delivery of the fluid comprising washing reagent. Such a separate supply channel and microfluidic channel structure may for example be similar, e.g. be a tree-like structure, to the structures described for the different deoxyribonucleotide triphosphate (dNTP) supplied.

The invention claimed is:

1. A microfluidic chip for use in multiplexed analysis of samples, the microfluidic chip comprising at least three stacked fluidic layers, the microfluidic chip further comprising a plurality of sensing chambers comprising at least a plurality first of sensing chambers, a first plurality of fluid supply channels, each of the fluid supply channels being configured to provide a different fluid, the first plurality of fluid supply channels comprising a first fluid supply channel configured to provide a first fluid, the first fluid supply channel comprising a branch point for each sensing chamber of the plurality of first sensing chambers, and a second fluid supply channel configured to provide a second fluid, the second fluid supply channel comprising a branch point for each sensing chamber of the plurality of first sensing chambers, and a first plurality of microfluidic channels, the first plurality of microfluidic channels comprising at least a plurality of first microfluidic channels, each of the first microfluidic channels being disposed in one or more of the fluidic layers of the microfluidic chip that is different than the fluidic layer in which the first fluid supply channel is disposed, each of the first microfluidic channels fluidly connecting the first fluid supply channel to one of the sensing chambers of the plurality of first sensing chambers, and being fluidly connected to the first fluid supply channel by a first via disposed between a first one of the one or more fluidic layers in which said first microfluidic channel is disposed and the fluidic layer in which the first fluid supply channel is disposed, at a branch point of the first fluid supply channel that is the closest branch point of the first fluid supply channel to the sensing chamber to which said first microfluidic channel fluidly connects the first supply channel; and a plurality of second microfluidic channels, each of the second microfluidic channels being disposed in one or more of the fluidic layers of the microfluidic chip that is different than a fluidic layer in which the second fluid supply channel is disposed, each of the second microfluidic channels fluidly connecting the second fluid supply channel to one of the sensing chambers of the plurality of first sensing chambers, and being fluidly connected to the second fluid supply channel by a first via disposed between a first one of the one or more fluidic layers in which said second microfluidic channel is disposed and the fluidic layer in which the second fluid supply channel is disposed, at a branch point of the second fluid supply channel that is the closest branch point of the second fluid supply channel to the sensing chamber to which said second microfluidic channel fluidly connects the second supply channel, wherein each sensing chamber of the plurality of first sensing chambers is fluidly connected to the first supply channel through one of the first microfluidic channels, and is fluidly connected to the first supply channel through one of the second microfluidic channels, and wherein each of the first sensing chambers is disposed in a fluidic layer of the microfluidic chip that is different than the first one of the one or more fluidic layers in which the corresponding first microfluidic channel is disposed, is different than the first one of the one or more fluidic layers in which the corresponding second microfluidic channel is disposed, is different than the fluidic layer in which the first fluid supply channel is disposed, and is different than the fluidic layer in which the second fluid supply channel is disposed, the fluid supply channels and the microfluidic channels thus forming a hierarchical delivery distribution system for supplying the fluids to the plurality of sensing chambers.

2. The microfluidic chip according to claim 1, further comprising a first common waste channel, the common waste channel having an output, the common waste channel being configured to remove fluid from the microfluidic chip, wherein each of the sensing chambers of the plurality of first sensing chambers is further in fluid communication with the common waste channel, the waste channel comprising an output.

3. The microfluidic chip according to claim 1, wherein the first fluid supply channel and the second fluid supply channel are substantially positioned in one of the fluidic layers of the microfluidic chip, and the plurality of first microfluidic channels and the plurality of second microfluidic channels are substantially positioned in one or more different fluidic layers of the microfluidic chip.

4. The microfluidic chip according to claim 1, wherein said fluid connection between each of the first sensing chambers and the first microfluidic channel connected thereto and the fluid connection between each of the first sensing chambers and the second microfluidic channel connected thereto are controllable using a valve.

5. The microfluidic chip according to claim 4, wherein said valve is controllable from outside the microfluidic chip.

6. A microfluidic sensing system, the sensing system comprising a microfluidic chip reader and the microfluidic chip according to claim 1, configured to cooperate with the microfluidic chip reader.

7. The microfluidic chip according to claim 1, wherein each of the first microfluidic channels and the second microfluidic channels comprises a first portion and a second portion, the second portion having a smaller cross-section than the first portion.

8. The microfluidic chip according to claim 1, wherein
each of the first microfluidic channels, comprises a first portion and a second portion, the second portion having a smaller cross-section than the first portion, the first portion being disposed in fluid communication between the first fluid supply channel and the second portion; and each of the second microfluidic channels, comprises a first portion and a second portion, the second portion having a smaller cross-section than the first portion, the first portion being disposed in fluid communication between the second fluid supply channel and the second portion.

9. The microfluidic chip according to claim 1, wherein
each of the first microfluidic channels comprises a first portion and a second portion, the second portion having a smaller cross-section than the first portion, the first portion being disposed in fluid communication between the first fluid supply channel and the second portion, the second portion being disposed in a different fluidic layer of the microfluidic chip than the first portion and in a same fluidic layer of the microfluidic chip as the sensing chamber that is fluidly connected to the first fluid supply channel by said first microfluidic channel, the second portion being connected to the first portion by a second via; and each of the second microfluidic channels comprises a first portion and a second portion, the second portion having a smaller cross-section than the first portion, the first portion being disposed in fluid communication between the second fluid supply channel and the second portion, the second portion being disposed in a different fluidic layer of the microfluidic chip than the first portion and in a same fluidic layer of the microfluidic chip as the sensing chamber that is fluidly connected to the second fluid supply channel by said second microfluidic channel, the second portion being connected to the first portion by a second via.

10. The microfluidic chip of claim 1, wherein the second fluid supply channel and the first microfluidic channel cross one another in different fluidic layers of the microfluidic chip.

11. The microfluidic chip of claim 1, wherein each of the plurality of first sensing chambers is fluidly connected to its respective first microfluidic channel and to its respective second microfluidic channel by a common sensing channel.

12. The microfluidic chip according to claim 1, wherein the sensing chamber is in a different fluidic layer of the microfluidic chip than its respective first microfluidic channel and its respective second microfluidic channel.

13. The microfluidic chip according to claim 1, wherein
the first supply channel and the second supply channel are in a first fluidic layer of the microfluidic chip;
the plurality of first microfluidic channels and the plurality of second microfluidic channels are in a second fluidic layer of the microfluidic chip; and the plurality of first sensing chambers are in a third fluidic layer of the microfluidic chip, the second fluidic layer being disposed between the first fluidic layer and the third fluidic layer.

14. The microfluidic chip according to claim 1, wherein
each first microfluidic channel comprises a first portion and a second portion, the first portion being fluidly disposed between the first fluid supply channel and the second portion;
each second microfluidic channel comprises a first portion and a second portion, the first portion being fluidly disposed between the second fluid supply channel and the second portion;
the first fluid supply channel and the second fluid supply channel are in a first fluidic layer of the microfluidic chip;
the first portion of each first microfluidic channel and the first portion of each second microfluidic channel are in a second fluidic layer of the microfluidic chip; and
the second portion of each first microfluidic channel, the second portion of each second microfluidic channel, and the plurality of first sensing chambers are in a third fluidic layer of the microfluidic chip, the second fluidic layer being disposed between the first layer and the third fluidic layer.

15. The microfluidic chip according to claim 1, wherein the plurality of sensing chambers further comprises a plurality of second sensing chambers, each of the second sensing chambers being fluidly connected to the first fluid supply channel by one of the first microfluidic channels, and fluidly connected to the second fluid supply channel by one of the second microfluidic channels.

16. The microfluidic chip according to claim 15, wherein
each first microfluidic channel comprises a first portion and a second portion, the first portion being fluidly disposed between the first fluid supply channel and the second portion;
each second microfluidic channel comprises a first portion and a second portion, the first portion being fluidly disposed between the second fluid supply channel and the second portion;
each third microfluidic channel comprises a first portion and a second portion, the first portion being fluidly disposed between the third fluid supply channel and the second portion;
the first fluid supply channel, the second fluid supply channel and the third fluid supply channel are disposed in a first fluidic layer of the microfluidic chip;
the first portion of each first microfluidic channel, the first portion of each second microfluidic channel, and the first portion of each third microfluidic channel are in a second fluidic layer of the microfluidic chip; and
the second portion of each first microfluidic channel, the second portion of each second microfluidic channel, the second portion of each third microfluidic channel, and the plurality of first sensing chambers are in a third fluidic layer of the microfluidic chip, the second fluidic layer being disposed between the first fluidic layer and the third fluidic layer.

17. The microfluidic chip according to claim 1, wherein the first plurality of supply channels further comprises
a third fluid supply channel configured to provide a third fluid, the third fluid supply channel comprising a branch point for each sensing chamber of the plurality of first sensing chambers; and
the first plurality of microfluidic channels further comprises
a plurality of third microfluidic channels, each of the third microfluidic channels being disposed in one or more of the fluidic layers of the microfluidic chip that is different than a fluidic layer in which the third fluid supply channel is disposed, each of the third microfluidic channels
fluidly connecting the third fluid supply channel to one of the sensing chambers of the plurality of first sensing chambers, and
being fluidly connected to the third fluid supply channel by a first via disposed between a first one of the one or more fluidic layers in which said third microfluidic channel is disposed and the fluidic layer in which the third fluid supply channel is disposed, at a branch point of the third fluid supply channel that is the closest branch point of the third fluid supply channel to the sensing chamber to which said third microfluidic channel fluidly connects the third supply channel,
wherein each of the first sensing chambers is disposed in a fluidic layer of the microfluidic chip that is different than the first one of the one or more fluidic layers in which the corresponding third microfluidic channel is disposed, and is different than the fluidic layer in which the third fluid supply channel is disposed.

18. The microfluidic chip according to claim 17, wherein each of the first microfluidic channels, the second microfluidic channels and the third microfluidic channels comprises a first portion and a second portion, the second portion having a smaller cross-section than the first portion.

19. The microfluidic chip according to claim 17, wherein
each of the first microfluidic channels, comprises a first portion and a second portion, the second portion having a smaller cross-section than the first portion, the first portion being disposed in fluid communication between the first fluid supply channel and the second portion;
each of the second microfluidic channels, comprises a first portion and a second portion, the second portion having a smaller cross-section than the first portion, the first portion being disposed in fluid communication between the second fluid supply channel and the second portion; and
each of the third microfluidic channels, comprises a first portion and a second portion, the second portion having a smaller cross-section than the first portion, the first portion being disposed in fluid communication between the third fluid supply channel and the second portion.

20. The microfluidic chip according to claim 17, wherein each of the first microfluidic channels comprises a first portion and a second portion, the second portion having a smaller cross-section than the first portion, the first portion being disposed in fluid communication between the first fluid supply channel and the second portion, the second portion being disposed in a different fluidic layer of the microfluidic chip than the first portion and in a same fluidic layer of the microfluidic chip as the sensing chamber that is fluidly connected to the first fluid supply channel by said first microfluidic channel, the second portion being connected to the first portion by a second via; each of the second microfluidic channels comprises a first portion and a second portion, the second portion having a smaller cross-section than the first portion, the first portion being disposed in fluid communication between the second fluid supply channel and the second portion, the second portion being disposed in a different fluidic layer of the microfluidic chip than the first portion and in a same fluidic layer of the microfluidic chip as the sensing chamber that is fluidly connected to the second fluid supply channel by said second microfluidic channel, the second portion being connected to the first portion by a second via; and each of the third microfluidic channels comprises a first portion and a second portion, the second portion having a smaller cross-section than the first portion, the first portion being disposed in fluid communication between the third fluid supply channel and the second portion, the second portion being disposed in a different fluidic layer of the microfluidic chip than the first portion and in a same fluidic layer of the microfluidic chip as the sensing chamber that is fluidly connected to the third fluid supply channel by said third microfluidic channel, the second portion being connected to the first portion by a second via.

21. The microfluidic chip of claim 17, wherein the second fluid supply channel and the first microfluidic channel cross one another in different fluidic layers of the microfluidic chip, and wherein the third fluid supply channel and the second microfluidic channel cross over one another in different fluidic layers of the microfluidic chip.

22. The microfluidic chip of claim 17, wherein each of the plurality of first sensing chambers is fluidly connected to its respective first microfluidic channel, to its respective second microfluidic channel, and to its respective third microfluidic channel by a common sensing channel.

23. The microfluidic chip according to claim 17, wherein the sensing chamber is in a different fluidic layer of the microfluidic chip than its respective first microfluidic channel and its respective second microfluidic channel.

24. The microfluidic chip according to claim 17, wherein
the first supply channel, the second supply channel, and the third supply channel are in a first fluidic layer of the microfluidic chip;
the plurality of first microfluidic channels, the plurality of second microfluidic channels, and the plurality of third microfluidic channels are in a second fluidic layer of the microfluidic chip; and
the plurality of first sensing chambers are in a third fluidic layer of the microfluidic chip, the second fluidic layer being disposed between the first fluidic layer and the third fluidic layer.

25. The microfluidic chip according to claim 17, wherein the plurality of sensing chambers further comprises a plurality of second sensing chambers, each of the second sensing chambers being fluidly connected to the first fluid supply channel by one of the first microfluidic channels, fluidly connected to the second fluid supply channel by one of the second microfluidic channels, and fluidly connected to the third fluid supply channel by one of the third microfluidic channels.

26. The microfluidic chip according to claim 17, wherein
the first plurality of supply channels further comprises
a fourth fluid supply channel configured to provide a fourth fluid, the fourth fluid supply channel comprising a branch point for each sensing chamber of the plurality of first sensing chambers; and
a fifth fluid supply channel configured to provide a fifth fluid, the fifth fluid supply channel comprising a branch point for each sensing chamber of the plurality of first sensing chambers;
the first plurality of microfluidic channels further comprises
a plurality of fourth microfluidic channels, each of the fourth microfluidic channels being disposed in a fluidic layer of the microfluidic chip that is different than a fluidic layer in which the fourth fluid supply channel is disposed, each of the fourth microfluidic channels
fluidly connecting the fourth fluid supply channel to one of the sensing chambers of the plurality of first sensing chambers, and
being fluidly connected to the fourth fluid supply channel by a first via disposed between the fluidic layer in which said fourth microfluidic channel is disposed and the fluidic layer in which the fourth fluid supply channel is disposed, at a branch point of the fourth fluid supply channel that is the closest branch point of the fourth fluid supply channel to the sensing chamber to which said fourth microfluidic channel fluidly connects the fourth supply channel; and
a plurality of fifth microfluidic channels, each of the fifth microfluidic channels being disposed in a fluidic layer of the microfluidic chip that is different than a fluidic layer in which the fifth fluid supply channel is disposed, each of the fifth microfluidic channels
fluidly connecting the fifth fluid supply channel to one of the sensing chambers of the plurality of first sensing chambers, and
being fluidly connected to the fifth fluid supply channel by a first via disposed between the fluidic layer in which said fifth microfluidic channel is disposed and the fluidic layer in which the fifth fluid supply channel is disposed, at a branch point of the fifth fluid supply channel that is the closest branch point of the fifth fluid supply channel to the sensing chamber to which said fifth microfluidic channel fluidly connects the fifth supply channel,
wherein each of the first sensing chambers is disposed in a fluidic layer of the microfluidic chip that is different than the first one of the one or more fluidic layers in which the corresponding fourth microfluidic channel is disposed, is different than the first one of the one or more fluidic layers in which the corresponding fifth microfluidic channel is disposed, is different than the layer in which the fourth fluid supply channel is disposed, and is different than the fluidic layer in which the fifth supply channel is disposed.

27. The microfluidic chip according to claim 26, wherein each of the first, second, third and fourth supply channels contains a different type of deoxyribonucleotide triphosphate fluid; and the fifth supply channel contains a fluid comprising washing reagent.

28. The microfluidic chip according to claim 26, wherein the plurality of sensing chambers further comprises a plurality of second sensing chambers, each of the second sensing chambers being fluidly connected to the first fluid supply channel by one of the first microfluidic channels, fluidly connected to the second fluid supply channel by one of the second microfluidic channels, fluidly connected to the third fluid supply channel by one of the third microfluidic channels, fluidly connected to the fourth fluid supply channel by one of the fourth fluid microfluidic channels, and fluidly connected to the fifth fluid supply channel by one of the fifth fluid microfluidic channels.

29. The microfluidic chip according to claim 1, wherein the microfluidic chip comprises a silicon substrate on which the fluidic layers are disposed.

30. The microfluidic chip according to claim 29, wherein the first fluid supply channel, the second fluid supply channel, the plurality of first microchannels, the plurality of second microchannels, and the plurality of first sensing chambers are formed in layers of silicon dioxide.

31. The microfluidic chip according to claim 1, further comprising a ring resonator operatively coupled to each sensing chamber.

32. A method for performing multiplexed analysis of samples based on microfluidics, the method comprising
providing the microfluidic chip according to claim 1,
delivering a first fluid from the first fluid supply channel, through the plurality of first microfluidic channels and into the plurality of first sensing chambers; and
delivering a second fluid from the second fluid supply channel, through the plurality of second microfluidic channels and into the plurality of first sensing chambers, and
sensing an interaction between a component in the sensing chamber and a component delivered with one or more of the fluids.

33. A method for performing multiplexed analysis of samples based on microfluidics, the method comprising:
providing a device according to claim 26;
providing a nucleic acid having a sequence to be characterized in each of the plurality of first sensing chambers;
using a first fluid comprising a first deoxyribonucleotide,
delivering the first fluid from the first fluid supply channel, through the plurality of first microfluidic channels and into the plurality of first sensing chambers, thereby allowing interaction between the first deoxyribonucleotide triphosphate and the sequence to be characterized at each of the plurality first of sensing chambers,
washing each of the plurality of first sensing chambers with a fluid comprising a washing reagent, and
sensing the interaction between the first deoxyribonucleotide triphosphate and the sequence to be characterized at each of the plurality of first sensing chambers;
using a second fluid comprising a second deoxyribonucleotide,
delivering the second fluid from the second fluid supply channel, through the plurality of second microfluidic channels and into the plurality of first sensing chambers, thereby allowing interaction between the second deoxyribonucleotide triphosphate and the sequence to be characterized at each of the plurality of first sensing chambers,
washing each of the plurality of first sensing chambers with a fluid comprising a washing reagent, and
sensing the interaction between the second deoxyribonucleotide triphosphate and the sequence to be characterized at each of the plurality of first sensing chambers.

34. The method according to claim 33, wherein each of the washing steps is performed by delivering the fluid comprising the washing reagent from the fifth fluid supply channel, through the plurality of fifth microfluidic channels and into the plurality of first sensing chambers.

35. The method according to claim 33, wherein the sensing is performed optically.

* * * * *